United States Patent [19]

Brändström

[11] Patent Number: 4,738,974

[45] Date of Patent: Apr. 19, 1988

[54] BASE ADDITION SALTS OF OMEPRAZOLE

[75] Inventor: Arne E. Brändström, Gothenburg, Sweden

[73] Assignee: Aktiebolaget Hässle, Sweden

[21] Appl. No.: 854,739

[22] Filed: Apr. 21, 1986

Related U.S. Application Data

[63] Continuation of Ser. No. 640,020, Aug. 10, 1984, abandoned, which is a continuation-in-part of Ser. No. 586,107, Mar. 5, 1984, abandoned.

[51] Int. Cl.$^4$ .................... C07D 401/12; A61K 31/44
[52] U.S. Cl. ...................................... 514/338; 546/271
[58] Field of Search ........................ 546/271; 514/338

[56] References Cited

U.S. PATENT DOCUMENTS

| | | | |
|---|---|---|---|
| 4,045,563 | 8/1977 | Berntsson et al. | 546/271 |
| 4,045,564 | 8/1977 | Berntsson et al. | 546/271 |
| 4,323,567 | 4/1982 | Narisada et al. | 544/90 |
| 4,472,409 | 9/1984 | Senn-Bilfinger | 546/271 |

FOREIGN PATENT DOCUMENTS

| | | |
|---|---|---|
| 0005129 | 10/1979 | European Pat. Off. |
| 0045200 | 2/1982 | European Pat. Off. |
| 1234058 | 6/1971 | United Kingdom |

OTHER PUBLICATIONS

*The Theory of Organic Chemistry, An Advanced Course*, by Gerald E. K. Branch, Ph.D and Melvin Calvin, Ph.D, Prentice-Hall, Inc. (1946).
*Heterocyclic Compounds*, vol. 5, Five-Membered Heterocycles Containing Two Hetero Atoms and Their Benzo Derivatives, edited by Robert C. Elderfield, John Wiley & Sons, Inc. (1952).
Derwent, 17863E (abstract).
K. A. Connors, G. L. Amidon and V. J. Stella: "Chemical Stability of Pharmaceuticals", second edition, John Wiley & Sons, New York, 1986, chapters 5 and 6.
J. T. Carstensen: "Pharmaceutics of Solids and Solid Dosage Forms", John Wiley & Sons, New York, 1977, chapter VII.
J. Tingstad and J. Dudzinski: "Preformulation Studies II: Stability of Drug Substances in Solid Pharmaceutical Systems", *J. Pharm. Sci.*, 62, 1973, 1856-1860.
S. M. Berge, L. D. Bighley and D. C. Monkhouse: "Pharmaceutical Salts", *J. Pharm. Sci.*, 66, 1977, 1-19.
H. V. Maulding, M. A. Zoglio, F. E. Pigois and M. Wagner: "Pharmaceutical Heterogeneous Systems IV: A Kinetic Approach to the Stability Screening of Solid Dosage Forms Containing Aspirin", *J. Pharm. Sci.*, 58, 1969, 1359-1362.
C. A. Kelly: "Determination of the Decomposition of Aspirin", *J. Pharm. Sci.*, 59, 1970, 1053-1079.
E. De Ritter, L. Magid, M. Osadca and S. H. Rubin: "Effect of Silica Gel in Stability and Biological Availability of Ascorbic Acid", *J. Pharm. Sci.*, 59, 1970, 229-232.
"Draft Guideline for Stability Studies for Human Drugs and Biologics", Mar. 1984, pp. 1-25.

*Primary Examiner*—Jane T. Fan
*Attorney, Agent, or Firm*—Brumbaugh, Graves, Donohue & Raymond

[57] ABSTRACT

Novel salts of omeprazole with Li$^+$, Na$^+$, K$^+$, Mg$^{2+}$, Ca$^{2+}$, Ti$^{4+}$, N$^+$(R$^1$)$_4$ or

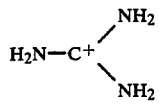

as cation; processes for their preparation thereof, pharmaceutical compositions containing such salts and their use in medicine.

20 Claims, No Drawings

BASE ADDITION SALTS OF OMEPRAZOLE

This application is a continuation of application Ser. No. 640,020, filed on 8/10/84, now abandoned, which is a continuation-in-part of application Ser. No. 586,107, filed on Mar. 5, 1984, now abandoned.

FIELD OF THE INVENTION

The invention relates to novel salts of the known compound omeprazole.

BACKGROUND OF THE INVENTION

The compound known under the generic name omeprazole, having the structural formula

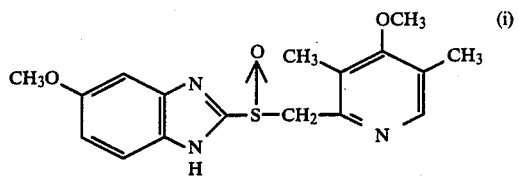

which is described i.a. in European patent specification 0005129, is being extensively investigated clinically as a gastric acid secretion inhibiting agent.

Omeprazole is useful for inhibiting gastric acid secretion as well as for providing gastrointestinal cytoprotective effects in mammals and man. In a more general sense, omeprazole may be used for prevention and treatment of gastrointestinal inflammatory diseases in mammals and man, including e.g. gastritis, gastric ulcer, and duodenal ulcer. Furthermore, omeprazole may be used for prevention and treatment of other gastrointestinal disorders where cytoprotective and/or gastric antisecretory effect is desirable, e.g. in patients with gastrinomas, in patients with acute upper gastrointestinal bleeding, and in patients with a history of chronic and excessive alcohol consumption.

The term "omeprazole" as used in this specification designates the neutral form of the compound of the formula (i), that is the form as given in the formula (i) without salt forming components present. A problem with omeprazole is its stability characteristics. Upon storage without any special precautions being taken, it is degraded at a rate which is higher than desired. A storage during accelerated conditions, that is at +37° C. and at a relative humidity of 80% for a period of 6 months, about 6% of the substance is converted to degradation products. While the rate of decomposition of omeprazole at normal storage conditions is lower, it is nevertheless desirable to obtain physical forms of omeprazole which exhibit improved stability. This need for more stable forms of omeprazole is apparent when considering the often considerable time periods involved from the synthesis of the active substance through its incorporation in pharmaceutical preparations, distribution of the finished product to pharmacies etc. up to the consumption of the preparation by the patient. The present invention provides such new forms of omeprazole which exhibit improved storage stability.

THE INVENTION

It has been found that the novel alkaline salts of omeprazole with the structural formula

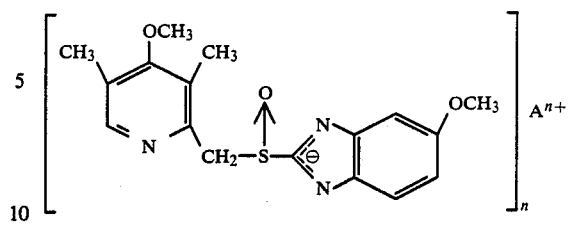

wherein n is 1,2, or 4; $A^{n+}$ is $Li^+$, $Na^+$, $K^+$, $Mg^{2+}$, $Ca^{2+}$, $Ti^{4+}$, $N^+(R^1)_4$ or

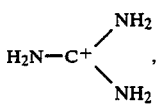

wherein $R^1$ is an alkyl group containing 1-4 carbon atoms are more stable during storage than the corresponding neutral form of omeprazole. The salts of the formula I are also easier to handle than the neutral form in the manufacture of pharmaceutical dosage units.

A preferred group of omeprazole salts of the formula I are those wherein $A^{n+}$ is $Na^+$, $K^+$, $Mg^{2+}$ and $Ca^{2+}$.

Further preferred salts are those wherein $A^{n+}$ is $Na^+$, $Mg^{2+}$ and $Ca^{2+}$. The $Na^+$-salt is especially preferred for the preparation of liquid pharmaceutical formulations, e.g. solutions for intravenous administration. The $Mg^{2+}$ and $Ca^{2+}$ salts are especially preferred for the preparation of tablets. The $Mg^{2+}$ salt is particularly preferred.

Illustrative examples of the alkyl group $R^1$ are $CH_3$, $C_2H_5$, $n-C_3H_7$, and $n-C_4H_9$.

The novel salts I of the invention are prepared by reacting omeprazole of the formula

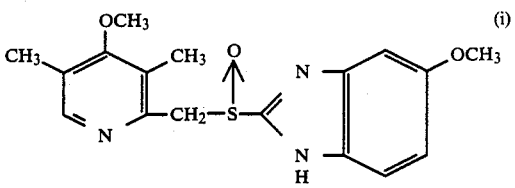

with a base capable of releasing the cation $A^{n+}$ (ii)

wherein $A^{n+}$ is as defined above, to give a salt of the formula

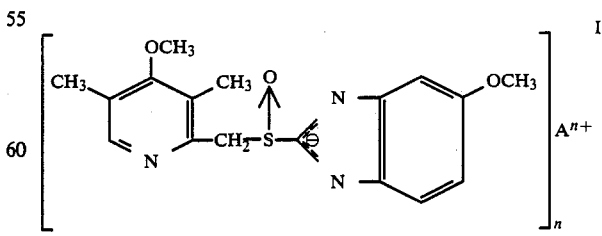

which salt is thereafter isolated.

Examples of bases capable of releasing the cation $A^{n+}$, and examples of reaction conditions are given below.

(a) Salts of the formula I wherein A is Li, Na or K are prepared by treating omeprazole with LiOH, NaOH or KOH in an aqueous or nonaqueous medium or with LiOR, LiNH$_2$, LiNR$_2$, NaOR, NaNH$_2$, NaNR$_2$, KOR, KNH$_2$ or KNR$_2$, wherein R is an alkyl group containing 1–4 carbon atoms, in a nonaqueous medium.

(b) Salts of the formula I wherein A is Mg, Ca, or Ti are prepared by treating omeprazole with Mg(OR)$_2$, Ca(OR)$_2$, CaH$_2$, Ti(OR)$_4$ or TiH$_4$, wherein R is an alkyl group containing 1–4 carbon atoms, in a nonaqueous solvent such as an alcohol (only for the alcoholates), e.g. ROH, or in an ether such as tetrahydrofuran. (c) Salts of the formula I wherein A is

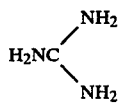

are prepared by treating omeprazole with the strong base

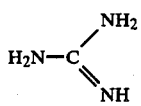

dissolved in a solvent, for example an alcohol.

(d) A salt of formula I may be converted to another salt of the same formula by exchanging the cation. When both the starting material and the salt obtained as final product are sufficiently soluble, such an exchange may be performed by using a cation-exchange resin saturated with the cation desired in the product. The exchange may also be performed by utilizing the low solubility of a desired salt. By this principle, for example, Na$^+$ as a counter ion may be exchanged for Ca$^{2+}$ or Mg$^{2+}$.

(e) The reaction between the compounds (i) and (ii) may also be carried out by ion-pair extraction. For example, tetrabutylammonium salts of the invention may be prepared by dissolving the Na$^+$-salt in water containing tetrabutylammonium sulfate followed by extraction of the tetrabutylammonium salt I into a methylene chloride phase, and subsequent isolation of the tetrabutylammonium salt I. In this manner also other tetraalkylammonium salts I may be prepared.

Illustrative examples of the radical R are CH$_3$, C$_2$H$_5$, n-C$_3$H$_7$, n-C$_4$H$_9$, i-C$_4$H$_9$, sec.-C$_4$H$_9$ and tert.-C$_4$H$_9$.

The invention also relates to pharmaceutical compositions containing a novel salt of omeprazole as active ingredient; to the use of the novel omeprazolesalts for providing local gastrointestinal cytoprotective effects in mammals and man; to the use of the novel omeprazole salts in the prevention and treatment of gastrointestinal inflammatory diseases in mammals and man; to the use of the novel omeprazole salts for inhibiting gastric acid secretion in mammals and man; to a method for inhibiting gastric acid secretion in mammals and man by administering a compound of the formula I; to a method for the treatment of gastrointestinal inflammatory diseases in mammals and man by administering a compound of the formula I; and to a method for providing gastrointestinal cytoprotective effects in mammals and man by orally administering a compound of the formula I.

For clinical use the compounds of the invention are formulated into pharmaceutical formulations for oral, rectal, parenteral or other mode of administration; however only oral administration is suitable for providing gastrointestinal cytoprotective effects. The pharmaceutical formulation contains a compound of the invention in combination with a pharmaceutically acceptable carrier. The carrier may be in the form of a solid, semisolid or liquid diluent, or a capsule. These pharmaceutical preparations are a further aspect of the invention. Usually the amount of active compound is between 0.1–95% by weight of the preparation, between 0.2–20% by weight in preparations for parenteral use and between 1 and 50% by weight in preparations for oral administration.

In the preparation of pharmaceutical formulations containing a compound of the present invention in the form of dosage units for oral administration the compound selected may be mixed with a solid, powdered carrier, e.g. lactose, saccharose, sorbitol, mannitol, starch, amylopectin, cellulose derivatives or gelatin, as well as with lubricating agents e.g. magnesium stearate, calcium stearate, sodium steryl fumarate and polyethylene glycol waxes. The mixture is then processed into granules or pressed into tablets. Since the compounds of the invention are susceptible to degradation in acid to neutral media, the above-mentioned granules or tablets when used for gastric acid inhibition are preferably coated with an enteric coating which protects the active compound from acid degradation as long as the dosage form remains in the stomach. The enteric coating is chosen among pharmaceutically acceptable enteric-coating materials e.g. beeswax, shellac or anionic film-forming polymers such as cellulose acetate phthalate, hydroxypropyl methylcellulose phthalate, partly methyl esterified methacrylic acid polymers and the like, if preferred in combination with a suitable plasticizer. To this coating various dyes may be added in order to distinguish among tablets or granules with different active compounds or with different amounts of the active compound present.

Soft gelatine capsules may be prepared with capsules containing a mixture of the active compound or compounds of the invention, vegetable oil, fat, or other suitable vehicle for soft gelatine capsules. Soft gelatine capsules are preferably enteric coated as described above. Hard gelatine capsules may contain enteric-coated granules of the active compound. Hard gelatine capsules may also contain the active compound in combination with a solid powdered carrier e.g. lactose, saccharose, sorbitol, mannitol, potato starch, corn starch, amylopectin, cellulose derivatives or gelatine; the hard gelatine capsules are preferably enteric coated as described above. In orally administering the compounds of the invention to provide gastrointestinal cytoprotective effects in mammals and man non-enteric coated oral dosage forms are usually preferred, however in order to achieve intestinal cytoprotection enteric coated dosage forms may be needed.

Dosage units for rectal administration may be prepared in the form of suppositories which contain the active substance mixed with a neutral fat base, or they may be prepared in the form of a gelatine rectal capsule which contains the active substance in a mixture with a vegetable oil, paraffin oil or other suitable vehicle for gelatine rectal capsules, or they may be prepared in the form of a ready-made micro enema, or they may be prepared in the form of a dry micro enema formulation to be reconstituted in a suitable solvent just prior to administration.

Liquid preparations for oral administration may be prepared in the form of syrups or suspensions, e.g. solutions or suspensions containing from 0.2% to 20% by weight of the active ingredient and the remainder consisting of sugar or sugar alcohols and a mixture of ethanol, water, glycerol, propylene glycol and polyethylene glycol. If desired, such liquid preparations may contain colouring agents, flavouring agents, saccharine and carboxymethyl cellulose and thickening agent. Liquid preparations for oral administration may also be prepared in the form of a dry powder to be reconstituted with a suitable solvent prior to use.

Solutions for parenteral administration may be prepared as a solution of a compound of the invention in a pharmaceutically acceptable solvent, preferably in a concentration from 0.1% to 10% by weight. These solutions may also contain stabilising agents and/or buffering agents and may be manufactured in unit dose ampoules or vials. Solutions for parenteral administration may also be prepared as a dry preparation to be reconstituted with a suitable solvent extemporaneously before use. Sodium salts of the invention are preferably used in the preparation of parenteral formulations.

The typical daily dose of the active substance varies within a wide range and will depend on various factors such as for example the individual requirement of each patient, the manner of administration and the disease. In general, oral and parenteral dosages will be in the range of 5 to 400 mg per day of active substance.

The following examples will further illustrate the invention.

EXAMPLE 1

Preparation of
5-methoxy-2-[[(4-methoxy-3,5-dimethyl-2-pyridinyl)-methyl]sulfinyl]-1H-benzimidazole sodium salt
(omeprazole sodium salt)

Omeprazole (1000 g, 2.90 mol) was added to a solution of NaOH (116 g, 2.90 mol) in deionized water (25 L). After stirring for 5 min methylene chloride (5 L) was added and stirring was continued for 10 min. The two phases were separated. The aqueous phase was washed with methylene chloride (5 L), filtered clear (Celite) and concentrated by evaporation under reduced pressure to about 2 L total volume. Absolute ethanol (6 L) was added and the evaporation was continued until dryness. Ethyl acetate (7 L) was added, the mixture was stirred under reflux for 30 min. After cooling and standing over night the resulting slurry was stirred with an additional amount (2 L) of ethyl acetate and filtered. The filter cake was washed with diethyl ether and dried under reduced pressure at 40° C. over night giving omeprazole sodium salt (975 g, 92%), mp 208°–210° C., NMR: $\delta(D_2O)$: 1.85(s, 3H), 2.1(s, 3H), 3.5(s, 3H), 3.85(s, 3H), 4.75(s, 2H), 6.85(dd, 1H), 7.2(d, 1H), 7.55(d, 1H), 8.15(d, 1H).

EXAMPLE 2

Preparation of omeprazole sodium salt

Omeprazole (1300 g, 3.77 mol) was added under vigorous mechanic stirring to a mixture of tetrahydrofuran (13 L) and 50% aqueous NaOH (296 g, 3.7 mol) and stirring was then continued for 45 min. Trichloroethylene (5.7 L) was added and stirring was continued over night at room temperature. The mixture was cooled to +5° C. and then stirred for 3 h. The precipitate was filtered off and the filter cake was washed with trichloroethylene (5 L) and dried under reduced pressure at 50° C. giving omeprazole sodium salt (1314 g, 95%), mp 208°–210° C.

EXAMPLE 3

Preparation of omeprazole potassium salt

Omeprazole (10.0 g, 0.0290 mol) was added to a solution of KOH (1.60 g, 0.0285 mol) in deionized water and then methylene chloride (50 ml) was added. The mixture was stirred vigorously for 15 min. The phases were separated and the aqueous phase was washed with methylene chloride (50 ml) and filtered clear (Celite). Evaporation to dryness gave a crystalline residue. Recrystallization from ethyl acetate yielded omeprazole potassium salt, mp. 148°–150° C. (soluble in water).

EXAMPLE 4

Preparation of di-omeprazole calcium salt dihydrate

Anhydrous $CaCl_2$ (17.9 g, 0.161 mol) dissolved in deionized water (200 ml) was added dropwise under viogorous stirring to a solution of omeprazole sodium salt (125 g, 0.340 mole) in deionized water (1250 ml) and then stirring was continued for 1 h at room temperature. The precipitate was centrifuged down and washed with deionized water until no $Cl^-$ was detectable ($AgNO_3$). After drying in the air and grinding, the crystals were dried in vacuum at 40° for 20 h yielding omeprazole calcium salt dihydrate (104 mg, 80%), mp 182°–184° C., NMR: $\delta(CDCl_3$ 1 drop of DMSO-$d_6$) 2.0(s, 3H), 2.15(s, 3H), 3.6(s, 3H), 3.7(s, 3H), 4.5(s, 2H), 6.7(dd, 1H), 7.1(d, 1H), 7.6(d, 1H, 8.15(s, 1H).

EXAMPLE 5

Preparation of di-omeprazole magnesium salt dihydrate

Anhydrous $MgCl_2$ (16.2 g, 0.17 mol) dissolved in deionized watr (625 ml) was added dropwise under vigorous stirring to a solution of omeprazole sodium salt (125 g, 0.340 mol) in deionized water (1560 ml) and then the stirring was continued for 1 h at room temperature. The precipitate was centrifugated down and then washed with deionized water until no $Cl^-$ was detectable ($AgNO_3$). Drying in the air, grinding and drying in vacuum at 40° for 24 h yielded omeprazole magnesium salt dihydrate (111 g, 87%) mp 177°–178° C.

EXAMPLE 6

Preparation of di-omeprazole magnesium salt

Magnesium (0.35 g, 0.0145 mol) was reacted with absolute methanol (10 ml) (in the presence of one drop of $CCl_4$) to give a solution of $Mg(OCH_3)_2$ in methanol solution. More methanol (10 ml) was added and the solution was added dropwise to a solution of omeprazole (10 g, 0.029 m) in methanol (200 ml) and the mixture was then stirred for 30 min at room temperature. Evaporation gave a crystalline solid of the di-omeprazole magnesium salt, mp. 178°–180°.

EXAMPLE 7

Preparation of omeprazole tetrabutylammonium salt

Omeprazole sodium salt (3.8 g, 0.010 mol) was added to a mixture of tetrabutylammonium hydrogensulphate (3.5 g, 0.010 mol) and NaOH (0.42 g, 0.0105 mol) in deionized water (15 ml). Methylene chloride (10 ml) was added and the mixture was shaken in a separatory funnel. After separation of the phases the organic phase was dried and the solvent evaporated off giving omeprazole tetrabutylammonium salt (3.5 g, 60%), NMR: $\delta(CDCl_3)$: 0.8–1.15(m, 12H), 1.15–1.6(m, 16H), 2.25(s, 3H), 2.3(s, 3H), 2.75–3.15(m, 8H), 3.75(s, 3H), 3.9(s, 3H), 4.7(d, 1H), 5.05(d, 1H), 6.8(dd, 1H), 7.3(d, 1H), 7.7(d, 1H), 8.35(s, 1H).

EXAMPLE 8

Preparation of omeprazole guanidinium $[C^+(NH_2)_3]$ salt

A solution of guanidine (0.0029 mol) [prepared from guanidinium nitrate and KOH] in ethanol (50 ml) was added to a solution of omeprazole (1.0 g, 0.0029 mol) and the resulting solution was stirred for 15 min. The solvent was evaporated giving omeprazole guanidinium salt, mp 110°–112° C. (soluble in water).

EXAMPLE 9

Preparation of tetra-omeprazole titanium salt

Titanium tetraisopropylate (1.03 g, 0.0036 mol) was added to a solution of omeprazole in dry isopropanol (250 ml) and the mixture was stirred under $N_2$ at room temperature for 4 h. (A white precipitate was formed). Evaporation of the solvent followed by washing 3 times with light petroleum and drying in vacuum gave a white crystalline powder of tetraomeprazole titanium salt, mp >260° C.

EXAMPLE 10

Preparation of omeprazole litium salt

Omeprazole (3.0 g, 0.0087 mol) was added to a solution of LiOH (0.207 g, 0.00865 mol) in deionized water and then methylene chloride (25 ml) was added. The mixture was stirred vigorously for 15 min. The phases were separated and the aqueous phase was washed with methylene chloride (25 ml) and filtered clear (Celite). Evaporation to dryness gave a crystalline omeprazole litium salt, mp. 198°–200° C. (soluble in water).

NMR: $\delta(CDCl_3)$ 1.65 (s, 3H), 1.8 (s, 3H), 3.45 (s, 3H), 3.4 (s, 3H), 4.2 (s, 2H), 6.6 (dd, 1H), 6.95 (d, 1H), 7.45 (d, 1H), 7.75 (s, 1H).

The NMR data given in the examples are measured at 90 MHz.

Incorporation of the novel omeprazole salts of the present invention in pharmaceutical preparations is exemplified in the following examples.

EXAMPLE 11

Syrup

A syrup containing 1% (weight per volume) of active substance was prepared from the following ingredients:

| I | Omeprazole sodium salt | 1.0 g |
|---|---|---|
|   | Sugar, powder | 30.0 g |
| II | Saccharine | 0.6 g |
|   | Glycerol | 5.0 g |
|   | Flavouring agent | 0.05 g |
|   | Ethanol | 5.0 g |
|   | Sorbic acid | 0.5 g |
|   | Sodium dihydrogen phosphate q.s. to pH= | 9.0 g |
|   | Distilled water q.s. to a final volume of | 100 ml |

I Powdered omeprazole sodium salt was carefully dry mixed with powdered sugar, dried in a vacuum oven over-night and dispensed into bottles each containing 31.0 gram of the powder mixture.
II A solution of saccharine, glycerol, flavouring agent, ethanol, sodium dihydrogen phosphate, sorbic acid and water was prepared, and dispensed into vials. When mixed with the powder mixture of omeprazole sodium salt and sugar the final volume was 100 ml.

Solvent vial II is to be added to powder mixture vial I just prior to use. The formed suspension is stable for ten days when stored at refrigerator temperature.

The salt given above may be replaced with another salt of the invention.

EXAMPLE 12

Enteric-coated tablets

An enteric-coated tablet containing 20 mg of active compound was prepared from the following ingredients:

| I | Omeprazole magnesium salt | 200 g |
|---|---|---|
|   | Lactose | 700 g |
|   | Methyl cellulose | 6 g |
|   | Polyvinylpyrrolidone cross-linked | 50 g |
|   | Magnesium stearate | 15 g |
|   | Distilled water | q.s. |
| II | Cellulose acetate phthalate | 200 g |
|   | Cetyl alcohol | 15 g |
|   | Isopropanol | 2000 g |
|   | Methylene chloride | 2000 g |

I Omeprazole magnesium salt, powder, was mixed with lactose, and granulated with a water solution of methyl cellulose. The wet mass was forced through a sieve and the granulate dried in an oven. After drying the granulate was mixed with polyvinylpyrrolidone and magnesium stearate. The dry mixture was pressed into tablet cores (10 000 tablets), each tablet containing 20 mg of active substance, in a tabletting machine using 6 mm diameter punches.
II A solution of cellulose acetate phthalate and cetyl alcohol in isopropanol/methylene chloride was sprayed onto the tablets I in an Accela Cota ®, Manesty coating equipment. A final tablet weight of 110 mg was obtained.

EXAMPLE 13

Solution for intravenous administration

A parenteral formulation for intravenous use, containing 4 mg of active compound per ml, was prepared from the following ingredients:

| I | Omeprazole sodium salt | 4.26 g |
|---|---|---|
|   | Sterile water | 200 ml |
| II | Polyethylene glycol 400 for injection | 400 g |
|   | Sodium dihydrogen phosphate | 1.5 g |
|   | Sterile water to a final volume of | 1000 ml |

I Omeprazole sodium salt 4.26 g, corresponding to 4.0 g of omeprazole, was dissolved in sterile water to a final volume of 200 ml. The solution was filtered through a 0.22μ filter and dispensed into sterile vials, each vial containing 2.0 ml. The vials were placed in a freeze drier with a shelf temperature of −40° C. When the solution in the vials had frozen, the solution was freeze dried. After drying the vials were stoppered.
II A solution of polyethylene glycol and sodium dihydrogen phosphate in sterile water was prepared, filtered through a 0.22μ filter, dispensed into sterile vials and the vials closed with a rubber stopper. The vials were sterilised in an autoclave at +120° C. for twenty minutes. Immediately before use 10.0 ml of solvent II is added to vial I. The clear solution contains 4 mg of omeprazole per milliliter.

TEST OF THE STABILITY OF OMEPRAZOLE SALTS OF THE INVENTION

The stability of omeprazole sodium salt, of the invention, obtained according to Example 1, was compared with the stability of the neutral form of omeprazole. Both test compounds were stored for six months at +37° C. and at a relative humidity of 80%. Thereafter, the amount of degradation products which had formed was measured. The result is given in Table 1 below.

TABLE 1

Stability of neutral omeprazole and of omeprazole sodium salt after six months storage at +37° C. and 80% relative humidity

| Test compound | Amount of degradation products formed (percent calculated on original amount of omeprazole) |
| --- | --- |
| neutral omeprazole | 6 |
| omeprazole sodium salt | 0.4 |

As seen in Table 1 the omeprazole sodium salt of the invention gave rise to substantially lower amounts of degradation products than the neutral form of omeprazole. This shows the improved stability of the novel omeprazole salts of the invention.

What I claim is:

1. A compound of the formula

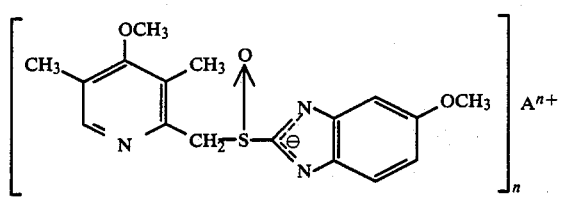

wherein n is 1, 2, or 4; and $A^{n+}$ is $Li^+$, $Na^+$, $K^+$, $Mg^{2+}$, or $Ca^{2+}$.

2. A compound according to claim 1 wherein $A^{n+}$ is $Na^+$, $K^+$, $Mg^{2+}$ or $Ca^{2+}$.

3. A compound according to claim 1 wherein $A^{n+}$ is $Na^+$.

4. A compound according to claim 1 wherein $A^{n+}$ is $Mg^{2+}$.

5. A pharmaceutical composition for inhibiting gastric acid secretion comprising a compound according to claim 1 in an amount effective to inhibit gastric acid secretion and a pharmaceutically acceptable carrier.

6. A pharmaceutical composition for inhibiting gastric acid secretion comprising a compound according to claim 2 in an amount effective to inhibit gastric acid secretion and a pharmaceutically acceptable carrier.

7. A pharmaceutical composition for inhibiting gastric acid secretion comprising a compound according to claim 3 in an amount effective to inhibit gastric acid secretion and a pharmaceutically acceptable carrier.

8. A pharmaceutical composition for inhibiting gastric acid secretion comprising a compound according to claim 4 in an amount effective to inhibit gastric acid secretion and a pharmaceutically acceptable carrier.

9. A method for inhibiting gastric acid secretion by administering to mammals an amount of a compound as defined in claim 1 sufficient to inhibit gastric acid secretion.

10. A method for inhibiting gastric acid secretion by administering to mammals an amount of a compound as defined in claim 2 sufficient to inhibit gastric acid secretion.

11. A method for inhibiting gastric acid secretion by administering to mammals an amount of a compound as defined in claim 3 sufficient to inhibit gastric acid secretion.

12. A method for inhibiting gastric acid secretion by administering to mammals an amount of a compound as defined in claim 4 sufficient to inhibit gastric acid secretion.

13. A method for the treatment of gastrointestinal inflammatory diseases in mammals by administering to mammals an amount of a compound as defined in claim 1 sufficient to treat gastrointestinal inflammatory disease.

14. A method for the treatment of gastrointestinal inflammatory diseases in mammals by administering to mammals an amount of a compound as defined in claim 2 sufficient to treat gastrointestinal inflammatory disease.

15. A method for the treatment of gastrointestinal inflammatory diseases in mammals by administering to mammals an amount of a compound as defined in claim 3 sufficient to treat gastrointestinal inflammatory disease.

16. A method for the treatment of gastrointestinal inflammatory diseases in mammals by administering to mammals an amount of a compound as defined in claim 4 sufficient to treat gastrointestinal inflammatory disease.

17. A method for providing gastrointestinal cytoprotective effects in mammals by administering to mammals an amount of a compound as defined in claim 1 sufficient to provide gastrointestinal cytoprotective effects.

18. A method for providing gastrointestinal cytoprotective effects in mammals by administering to mammals an amount of a compound as defined in claim 2 sufficient to provide gastrointestinal cytoprotective effects.

19. A method for providing gastrointestinal cytoprotective effects in mammals by administering to mammals an amount of a compound as defined in claim 3 sufficient to provide gastrointestinal cytoprotective effects.

20. A method for providing gastrointestinal cytoprotective effects in mammals by administering to mammals an amount of a compound as defined in claim 4 sufficient to provide gastrointestinal cytoprotective effects.

* * * * *

UNITED STATES PATENT AND TRADEMARK OFFICE
CERTIFICATE OF CORRECTION

PATENT NO. : 4,738,974

DATED : April 19, 1988

INVENTOR(S) : Arne Elof Brandstrom

It is certified that error appears in the above-identified patent and that said Letters Patent is hereby corrected as shown below:

<u>First page, after Item 63</u> insert -- [30] Foreign Application Priority Data

Mar. 4, 1983 [SE]  Sweden  8301182.5 --.

Signed and Sealed this

Twenty-seventh Day of December, 1988

Attest:

DONALD J. QUIGG

Attesting Officer         Commissioner of Patents and Trademarks